United States Patent [19]

Horiuchi

[11] Patent Number: 4,621,057
[45] Date of Patent: Nov. 4, 1986

[54] N-ACETYLHEXOSAMINE OXIDASE AND PROCESS FOR PRODUCING THE SAME

[75] Inventor: Tatsuo Horiuchi, Noda, Japan

[73] Assignee: Noda Institute for Scientific Research, Japan

[21] Appl. No.: 580,243

[22] Filed: Feb. 15, 1984

[30] Foreign Application Priority Data

Feb. 28, 1983 [JP] Japan ................................. 58-30801

[51] Int. Cl.⁴ .......................... C12N 9/06; C12R 1/38
[52] U.S. Cl. .................................... 435/191; 435/874
[58] Field of Search .................... 435/189, 191, 25, 28

[56] References Cited

FOREIGN PATENT DOCUMENTS 59-156281  9/1984  Japan ................................. 435/191
59-156299  9/1984  Japan ..................................... 435/25

*Primary Examiner*—Lionel M. Shapiro

*Attorney, Agent, or Firm*—Banner, Birch, McKie & Beckett

[57] ABSTRACT

An N-acetylhexosamine oxidase having the following physiochemical properties.

(1) Action and specificity for substrate

Oxidizes N-acetylhexosamine in the presence of oxygen to form N-acetylhexosaminic acid and hydrogen peroxide. Hardly acts or does not act at all on hexose and hexosamine.

(2) Optimum pH and stable pH range

When a potassium phosphate buffer solution contining 0.1M glycine is used, an optimum pH is 7.5 to 8.5 and a stable pH range is 3 to 9.

(3) Molecular weight

Has a molecular weight of about 140,000 to 150,000 when measured according to a gel filtration method using Sephadex G-200 by the use of 0.05M potassium phosphate buffer solution.

4 Claims, 5 Drawing Figures

N-ACETYLHEXOSAMINE OXIDASE AND PROCESS FOR PRODUCING THE SAME

This invention relates to a novel N-acetylhexosamine oxidase which oxidizes N-acetylhexosamine in the presence of oxygen to form N-acetylhexosaminic acid and hydrogen peroxide, as well as to a process for producing said enzyme.

It has been clarified recently that canceration of cells due to viruses changes glycides of outermost layers of cells including N-acetylglucosamine. It has been confirmed that in liver cancer, a glucosamine-6-phosphoric acid synthesis enzyme (glucosamine phosphate isomerase) which is a restricting enzyme for biosynthesis system of N-acetylglucosamine and N-acetylneuraminic acid shows a very high activity. Further, it has been known that in a certain kinds of blood cancers, lysozyme has a strikingly increased activity. Thus, activity change of the enzyme system having a close connection with N-acetylglucosamine and its derivatives has become to be used in medical check as an inspection item for predicting conditions of diseases. Presently, development of an enzyme which can quantitatively determine the above enzyme system easily, at a high precision and efficiently is desired strongly in the art.

The present inventor examined a wide variety of microorganisms to search for N-acetylhexosamine-decomposing bacteria. As a result, it has been found that bacteria belonging to the genus Pseudomonas produce a novel N-acetylhexosamine oxidase. Based on this finding, the present invention has been completed.

An object of this invention is to provide a novel N-acetylhexosamine oxidase and a process for producing the oxidase.

Other objects and advantages of the this invention will be made clear by the following description.

According to the present invention, there is provided a novel N-acetylhexosamine oxidase. According to the present invention, there is also provided a process for producing an N-acetylhexosamine oxidase which comprises culturing in a medium bacterial strains belonging to the genus Pseudomonas and having an ability of producing an N-acetylhexosamine oxidase and then collecting the N-acetylhexosamine oxidase from the culture products.

In the accompanying drawings.

The present enzyme has the following physicochemical properties.

(1) Action and specificity for substrate

As shown in the following reaction formula, the present enzyme oxidizes N-acetylhexosamine in the presence of oxygen to form N-acetylhexosaminic acid and hydrogen peroxide. The present enzyme hardly acts or does not all act on hexose, hexosamine and N-acetylneuraminic acid.

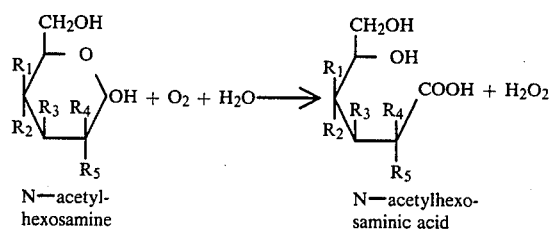

N—acetylhexosamine → N—acetylhexosaminic acid

Incidentally, specific examples of N-acetylhexosamines are shown in Table 1.

TABLE 1

| N—acetylhexosamines | $R_1$ | $R_2$ | N—acetylhexasamines $R_3$ | $R_4$ | $R_5$ |
|---|---|---|---|---|---|
| N—acetylglucosamine | —H | —OH | —OH | —H | —NHCOCH$_3$ |
| N—acetylgalactosamine | —OH | —H | —OH | —H | —NHCOCH$_3$ |
| N—acetyl muramic acid | —H | —OH | O—<br>\|<br>CH$_3$CHCOOH | —H | —NHCOCH$_3$ |
| N,N—diacetylchitobiose | —H | CH$_2$OH<br>—O<br>OH O<br>OH<br>NHCOCH$_3$ | —OH | —H | —NHCOCH$_3$ |
| N—acetylmanosamine | —H | —OH | —OH | —NHCOCH$_3$ | —H |

(2) Optimum pH and stable pH range

Figure 1:
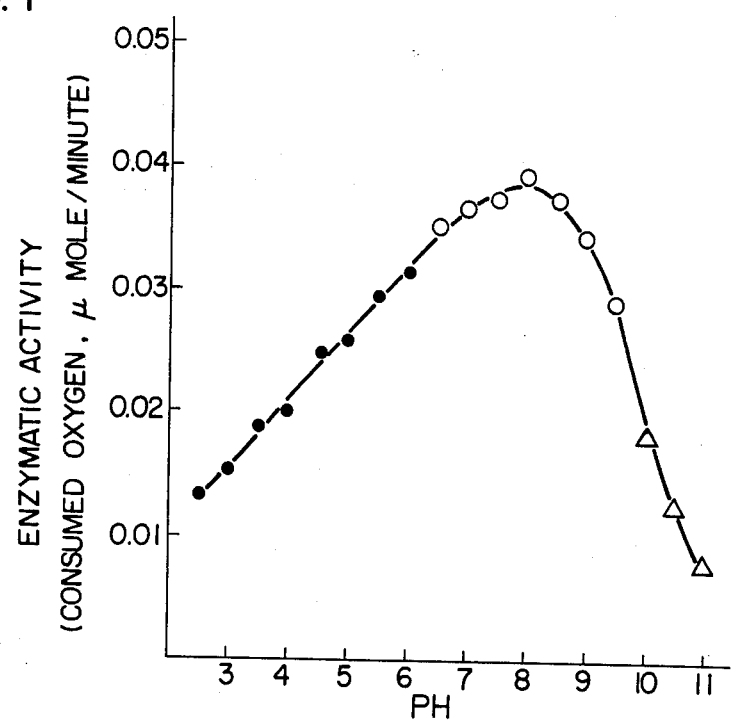
FIG. 1 shows an optimum pH range of the present enzyme.
Figure 2:
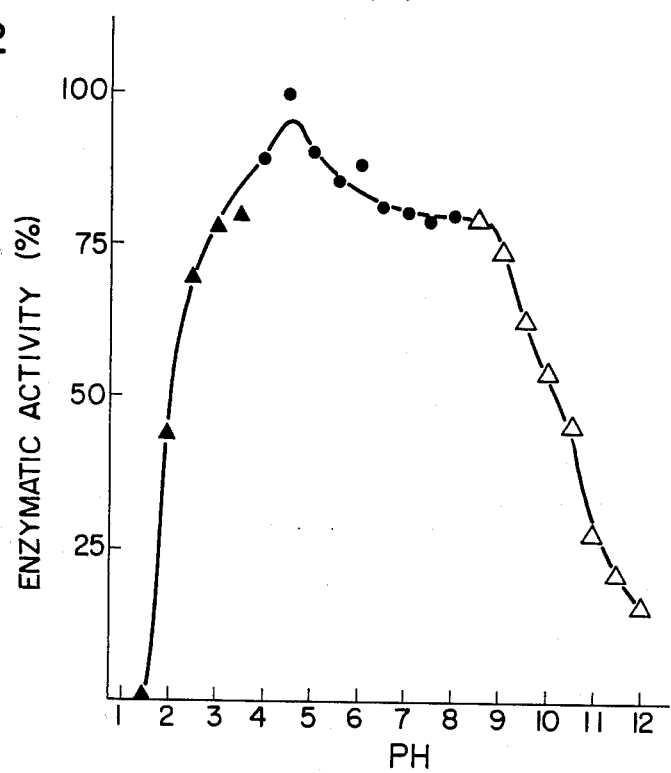
FIG. 2 shows a pH range in which the present enzyme is stable.

When a potassium phosphate buffer solution containing 0.1M glycine is used, the optimum pH of the present enzyme is 7.5 to 8.5. As an example, the activity of the present enzyme for N-acetylglucosamine was measured by the use of a citric acid sodium phosphate buffer solution, a potassium phosphate buffer solution containing 0.1M glycine and a glycine-sodium hydroxide buffer solution and the result obtained is shown in FIG. 1, in which the optimum pH of the present enzyme is 7.5 to 8.5. The measurement was made in the citric acid-sodium phosphate buffer solution, the potassium phosphate buffer solution containing 0.1M glycine and the glycine-sodium hydroxide buffer solution, in accordance with a consumed oxygen method. The pH range in which the present enzyme is stable is 3 to 9 as shown in FIG. 2. This stable pH range was measured by employing a hydrogen peroxide method and by dissolving the present enzyme in 0.1 ml of a citric acid-sodium phosphate buffer solution and a glycine-hydrochloric acid or sodium hydroxide buffer solution, heat-treating the resulting solution for 10 minutes at 45° C. and then measuring the residual activity of the enzyme.

Note: Measurement of enzymatic activity (a) By measuring oxygen consumed

In a closed vessel there are placed 2.9 ml of 0.1M potassium phosphate buffer solution of pH 8.0 containing 0.1M glycine and 0.1 ml of 0.5M N-acetylglucosamine solution. Then, an oxygen electrode manufactured by YSI Company of U.S.A. is inserted therein. While the content of the reaction vessel is being stirred at 37° C., 10 μl of the present enzyme in liquid form is added thereto to start a reaction. The amount of oxygen consumed is measured periodically by the use of an oxygen monitor manufactured by YSI Company. Incidentally, an enzymatic activity of consuming 1 μmol of oxygen per minutes is taken as 1 enzyme unit.

(b) By measuring hydrogen peroxide produced

In 0.1M potassium phosphate buffer solution of pH 6.8, are dissolved 0.005% of 4-aminoantipyrine, 0.02% of N,N-dimethylaniline and peroxidase. To 2.8 ml of the resulting solution in which peroxidase activity is 4 units, are added 0.1 ml of 0.5M N-acetylglucosamine and 0.1 ml of the present enzyme in liquid form to make the total volume 3 ml. The resulting mixture is subjected to reaction for 10 minutes at 37° C. Then, absorption at visible region (550 nm) is measured for the pigment produced, and the amount of hydrogen peroxide produced is calculated by the use of a standard curve.

(c) By measuring N-acetylhexosaminic acid produced

To 2.8 ml of 0.1M potassium phosphate buffer solution of pH 8.0, is added 0.1 ml of 0.5M N-acetylglucosamine. Then, thereto is added 0.1 ml of the present enzyme of liquid form. The resulting mixture is subjected to reaction for 10 minutes at 37° C. An appropriate volume of the reaction mixture is subjected to high performance liquid chromatography [column: TSK-GEL LS-220 manufactured by Toyo Soda; column size: 4 mm φ×250 mm L; mobile phase: 0.03M sodium chloride-0.025M sodium phosphate buffer solution of pH 7.0; temperature: 40° C.; detection: UV 220 nm], for separation of N-acetylglucosaminic acid. By comparing the height of the peak obtained with that of a standard product, N-acetylglucosaminic acid is determined quantitatively.

(3) Temperature range suitable for action

Figure 3:
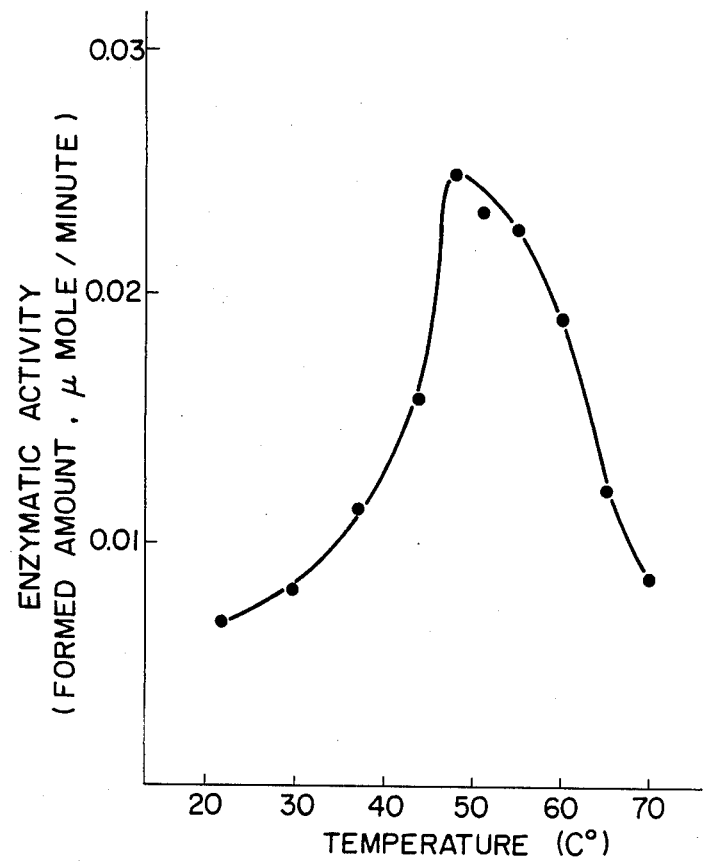
FIG. 3 shows a temperature range suitable for action of the present enzyme.

As shown in FIG. 3, a temperature range suitable for action of the present enzyme is 30° to 70° C. according to the result of measurement of the amount of N-acetylglucosaminic acid separated by the use of high performance liquid chromatography. This experiment was conducted by measuring the amount of produced N-acetylglucosaminic acid at each temperature in accordance with the method for quantitatively determining N-acetylhexosaminic acid.

(4) Deactivation conditions such as pH and temperature

Figure 4:
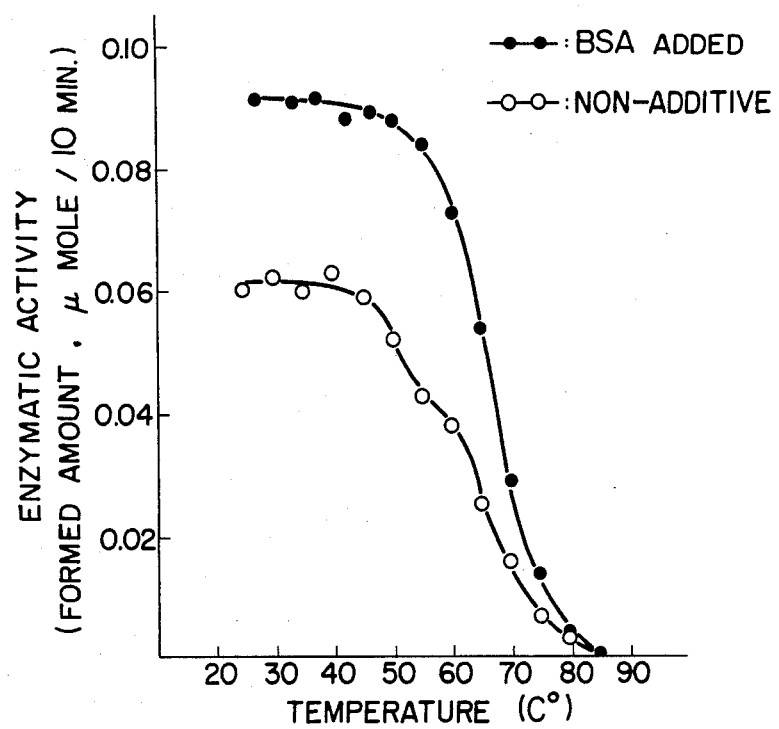
FIG. 4 shows deactivation of the present enzyme at each temperature.

As shown in FIG. 4, in 10 minutes heat treatment, deactivation of the present enzyme begins at 45° C. but the present enzyme retains about half of its activity even at 65° C. Further, in 10 minutes heat treatment at 45° C., the present enzyme is stable between pH 3 and pH 9 and loses its activity rapidly at a more acidic region and slowly at a more alkaline region. In this experiment, the hydrogen peroxide method was adopted, and the residual activity of the present enzyme subjected to 10 minutes heat treatment in a potassium phosphate buffer solution of pH 6.8 at each temperature was compared with the residual activity of the same enzyme subjected to the same treatment in a potassium phosphate buffer solution of pH 6.8 containing 1 mg/ml of bovine serum albumin.

(5) Activity inhibition and activity stabilization

The activity of the present enzyme was measured in various solutions each comprising a tris-hydrochloric acid buffer solution of pH 7.5 and 1.8mM metalic ion or inhibitor. The results are shown in Table 2. As is obvious from Table 2, the activity is inhibited greatly by iron (bivalent), mercury and zinc, and considerably by cadmium, lead and nickel.

Meanwhile, as shown in FIG. 4, the activity of the present enzyme is stabilized and moreover slightly enhanced by addition of bovine serum albumin.

TABLE 2

| Inhibitor | Residual activity (%) | Inhibitor | Residual activity (%) |
|---|---|---|---|
| No addition | 100 | | |
| Pb(CH$_3$COO)$_2$ | 42 | KCN | 95 |
| HgCl$_2$ | 17 | FCH$_2$COONa | 107 |
| AgNO$_3$ (Phosphate buffer solution) | 5 | EDTA[1] | 87 |
| ZnSO$_4$ | 2 | PCMB[2] | 67 |
| FeSO$_4$ | 15 | ICH$_2$CONH$_2$ | 90 |
| CdSO$_4$ | 52 | O'-Phenanthroline | 81 |
| NiSO$_4$ | 64 | 8-Hydroxyquinoline | 102 |
| CuSO$_4$ | 74 | α,α'-Dipyridyl | 106 |
| CoSO$_4$ | 75 | SDS[3] | 87 |
| MgSO$_4$ | 86 | | |
| CaCl$_2$ | 91 | | |
| MnSO$_4$ | 84 | | |
| NaN$_3$ | 103 | | |

[1]EDTA: Etheylenediaminetetracetic acid sodium salt
[2]PCMB: p-Chloromercurybenzoate
[3]SDS: Sodium dodecylsulfate (6) Purification The present enzyme can be separated and purified according to a usual method. For example, purification methods such as the column chromatography by a CM-cellulose column, the fractional precipitation method by ammonium sulfate, the column chromatography by a CM-Sephadex column, the gel filtration method by Sephadex and the like are used alone or in appropriate combinations.

(7) Molecular weight

The present enzyme has a molecular weight of about 140,000 to 150,000 when measured in accordance with the gel filtration method by a Sephadex G-200 column using 0.05M potassium phosphate buffer solution containing 0.1M sodium chloride.

(8) Electrophoresis by a polyacrylamide gel

Figure 5:
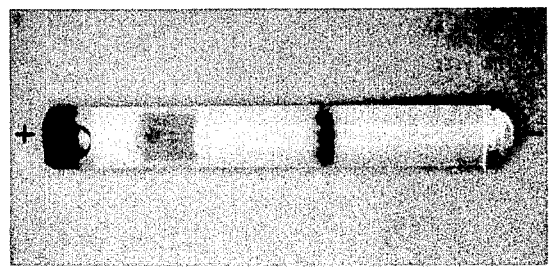
FIG. 5 shows an acrylamide disc electrophoresis of the present enzyme.

Polyacrylamide disc electrophoresis was conducted by using a gel (pH 4.0) of a polyacrylamide having 7.5% acrylamide concentration in accordance with a usual method. As a result, as shown in FIG. 5, a single band was observed.

(9) Isoelectric point

The isoelectric point of the present enzyme is 8.0 when measured by the polyacrylamide gel isoelectric focusing method.

(10) Analysis of amino acids

The following numbers represent molecule numbers of each amino acid present in one molecure of the present enzyme.

Aspartic acid 133, threonine 83, serine 72, glutamic acid 103, glycine 137, alanine 152, ½ cystine 28, valine 99, methionine 22, isoleucine 44, leucine 120, tyrosine 52, phenylalanine 38, lysine 49, histidine 37, arginine 78, tryptophane 18, proline 83.

As understood from the above, the present enzyme is a novel enzyme unknown to date, in its action and specificity for substrate.

Next, a process for producing an N-acetylhexosamine oxidase of the present invention will be explained.

Microorganisms used for producing the present enzyme are strains belonging to the genus Pseudomonas and having an ability of producing an N-acetylhexosamine oxidase. As one example of the strains, there is mentioned Pseudomonas sp. No. 15-1. Variants or mutants of this bacterium can be used also. Pseudomonas sp. No. 15-1 is the strain separated from a soil by the present inventor and has the following bacteriological properties.

(A) Form

Microscopic observation after culture in a bouillon-agar medium for 16 hr at 30° C.

(1) Cell size: A bacillus having a cell size of 0.5 to 0.8 micron by 1.0 to 1.3 micron.
(2) Polymorphism of cell: Not observed.
(3) Mobility: The present bacterium has polar flagella and accordingly mobility.
(4) Spore: Not formed.
(5) Gram-staining: Negative
(6) Acid-fast: Negative

(B) Growth in various media (1) Bouillon-agar plate culture: In 24 hr culture at 30° C., there appears a light yellowish brown and transparent colony having a smooth surface and a dim luster. No pigment is formed.
(2) Bouillon-agar slant culture: Growth is good. The same result as explained in above (1) is obtained.
(3) Bouillon liquid culture: Growth is uniform and good.
(4) Bouillon-gelatin stab culture: In 4 days culture at 30° C., slight growth is seen and there appears liquefaction of the culture medium
(5) Litmuth milk: Change to slightly alkaline.

(C) Physiological properties (1) Reduction of nitrate: Negative
(2) Denitrogenating reaction: Negative
(3) MR test: Negative
(4) VP test: Negative
(5) Indole formation: Negative
(6) H₂S formation: Negative
(7) Hydrolysis of starch: Negative
(8) Utilization of citric acid: Utilizes citric acid in both of Koser and Christensen media.
(9) Utilization of inorganic nitrogen sources: Utilizes ammonia but does not utilize nitrates.
(10) Pigment formation: Negative
(11) Urease: Negative
(12) Oxidase: Positive
(13) Catalase: Positive
(14) Growth conditions: Optimum pH range is 5 to 8. Optimum temperature range is 30° to 38° C.
(15) Behavior toward oxygen: Aerobic
(16) O-F test: Oxidative
(17) Formation of acids and gases from saccharides

| Saccharide   | Acid formation | Gas formation |
| ------------ | -------------- | ------------- |
| L-arabinose  | +              | −             |
| D-xylose     | +              | −             |
| D-glucose    | +              | −             |
| D-mannose    | −              | −             |
| D-fructose   | +              | −             |
| D-galactose  | +              | −             |
| Maltose      | −              | −             |
| Saccharose   | −              | −             |
| Lactose      | −              | −             |
| Trehalose    | −              | −             |
| D-sorbitol   | −              | −             |
| D-mannitol   | −              | −             |
| Inositol     | −              | −             |
| Glycerine    | −              | −             |
| Starch       | −              | −             |

(D) Other properties (1) In a medium limited in quantity of nitrogen sources, accumulates poly-β-hydroxybutyric acid esters in cells.
(2) Can not grow by using only DL-arginine and betaine as carbon sources.
(3) Grows at 41° C.
(4) Does not utilize hydrogen as an energy source.

The above bacteriological properties of the novel bacterium of the present invention having an ability of producing an oxidase for N-acetylhexosamine are compared with the classification of "Bergey's Manual of Determinative Bacteriology" (8th edition, 1974). The present bacterium shows negative Gram-staining, is an aerobic sporeless bacillus, has polar flagella and accordingly mobility, and is positive for catalase and oxidase; and accordingly belongs to the genus Pseudomonas and is classified into Section 3 and, because it grows at 41° C., appears to be identical with *Pseudomonas lemoignei*, however, is entirely different from *Pseudomonas lemoignei* in liquefaction of gelatin, utilization of saccharides, etc. Based on these facts, the present bacterium has been named as Pseudomonas sp. No. 15-1. Incidentally, the strain Pseudomonas sp. No. 15-1 was deposited internationally as FERM BP-227 on Dec. 21, 1982, in the Fermentation Research Institute, Agency of Industrial Science and Technology, Japan, in accordance with Budapest Treaty on the International Recognition of the Deposit of Microorganisms for the Purposes of Patent Procedure.

As the medium to be used in the present invention, synthetic media as well as natural media can be used as long as they contain carbon sources, nitrogen sources, inorganic matters and other nutrients appropriately. As carbon sources, there can be used glucose, galactose, fructose, xylose, arabinose, etc. and further glycine, mannitol, propionic acid, glycolic acid, lactic acid, etc. As nitrogen sources, there can be used preferably ammonium salts, proteinous digests such as peptone digest, casein digest and the like, and nitrogen-containing organic matters such as yeast extract and the like. As inorganic matters, there can be used salts of sodium, potassium, manganese, magnesium, calcium, cobalt, nickel, iron, copper, zinc and other metals. In the present invention, the yield of N-acetylhexosamine oxidase becomes highest when the strain having an ability of producing an N-acetylhexosamine oxidase is cultured in a medium containing N-acetylhexosamine. Preferable examples of such a culture medium include, for example, a medium of pH 6.5 containihg 0.5% of N-acetylglucosamine, 0.4% of yeast extract, 0.15% of polypeptone, 0.5% of glycerine, 0.05% of magnesium sulfate and 0.2% of potassium secondary phosphate. When a culture is conducted in this medium for 20 hr at 30° C. with stirring by air, the produced activity for N-acetylhexosamine oxidase is ten- to fifty-fold compared with when the same culture is made by replacing N-acetylglucosamine with glucose. The culturing temperature usually is in the range of 20° to 40° C., preferably 33° to 38° C. PH at the start of culture usually is in the range of 6 to 8, preferably about 7. By conducting a shaking culture or a submerged stirring culture for 18 to 24 hr under the above conditions, an N-acetylhexosamine oxidase is formed and accumulates in the culture products.

The N-acetylhexosamine oxidase formed above is present usually within bacterial cells. Therefore, the culture products are collected by centrifugation or filtration and then the bacterial cells are destroyed in an appropriate amount of a buffer solution, whereby the enzyme is dissolved and released into the solution. For destruction of the bacterial cells, (a) physical methods using an apparatus such as Dyno mill, French press, ultrasonic wave and the like, (b) chemical methods using chemicals such as Triton X-100, sodium laury sulfate, EDTA and the like, and (c) enzymatic methods using an enzyme such as lysozyme and the like can be used alone or in combination. The thus obtained solution wherein the bacterial cells are present in destroyed form is freed of nucleic acids in an ordinary manner and then freed of insolubles by filtration or centrifugation to obtain an N-acetylhexosamine oxidase. This N-acetylhexosamine oxidase is purified, if necessary, by an ordinary method for enzyme separation and purification, for example, by single or combination use of (1) a column chromatography by CM-cellulose column, (2) a fractional precipitation method by ammonium sulfate, (3) a column chromatography by CM-Sephadex column, (4) a gel filtration method by Sephadex and (5) any other appropriate method, whereby a purified N-acetylhexosamine oxidase can be obtained.

The use of the novel N-acetylhexosamine oxidase of the present invention enables quantitative determination with precision for compounds such as N-acetylglucosamine. Thereby, the activity of a glucosamine-6-phosphoric acid synthesis enzyme can be known and ultimately, based on the activity, conditions of various diseases can be grasped efficiently.

The present invention will be explained in more detail below by way of an Example, however, is in no way restricted to the Example.

EXAMPLE 1

Pseudomonas sp. No. 15-1 (FERM BP-227) was inoculated into 100 ml of a seed medium of pH 6.5 having a composition of 5 g/l of N-acetylglucosamine, 4 g/l of yeast extract, 1 g/l of potassium phosphate and 0.5 g/l of magnesium sulfate, in a 500 ml flask. Then, culture was conducted for 8 hr at 30° C. The thus obtained seed culture liquid was inoculated into 20 l of an enzyme production medium of pH 6.5 having a composition of 5 g/l of N-acetylglucosamine, 4 g/l of yeast extract, 5 g/l of glycerine, 1.5 g/l of polypeptone, 2 g/l of dipotassium hydrogenphosphate and 0.5 g/l of magnesium sulfate, in a 30 l jar fermenter. Culture was conducted for 20 hr at 35° C. with stirring (300 rpm) and aeration (20 l/min). Then, the culture liquid was subjected to contrifugation (12,000 rpm) to collect bacterial cells. To 411 g of the bacterial cells collected, was added 2 l of 0.05M potassium phosphate buffer solution of pH 7.0 to disperse the bacterial cells thoroughly. Thereto was added 200 ml of 10% aqueous Triton X-100 solution and thorough stirring was applied. Further, thereto was added 2.5 l of 0.05M potassium phosphate buffer solution of pH 7.0, and the mixture was allowed to stand overnight at low temperatures. Then, a saturated protamine sulfate solution of pH 7.5 was added until no more precipitate appeared. The precipitate was removed by centrifugation (2000 rpm) and the supernatant was condensed by the use of a hollow fiber ultrafiltration apparatus. The condensate was dialyzed against 0.05M acetic acid buffer solution using a cellulose tube, then adsorbed in a column (10.5 cm $\phi \times 40$ cm L) packed with CM-cellulose equilibrated with the same buffer solution and finally eluted by KCl eluting solutions having a concentration gradient of 0 to 0.6M KCl.

The active fractions eluted were put together and condensed to 400 ml by the use of a hollow fiber ultrafiltration apparatus. To the condensate, was added ammonium sulfate so that the latter became 30% saturation and the insolubles were removed by centrifugation. Further, ammonium sulfate was added so that it became 55% saturation and the resulting precipitate was collected by centrifugation and dissolved in 50 ml of 0.05M potassium phosphate buffer solution of PH 6.8 containing 35% saturation ammonium sulfate. The resulting insolubles were removed by centrifugation. The thus obtained solution was equilibrated with the same buffer solution in which the concentration of ammonium sulfate was 35% saturation. Then, the solution was subjected to adsorption in a column (4 cm $\phi \times 15$ cm L) packed with Phenyl Sepharose CL-4B manufactured by Pharmacia Co., Sweden. Elution was conducted by the use of 0.05M potassium phosphate buffer solutions of pH 6.8 having a concentration gradient (0 to 30%) of ethylene glycol and a reverse concentration gradient (20% saturation to 0) of ammonium sulfate. The active fractions eluted were collected and condensed by using an ultrafiltrating membrane. The condensate was dialyzed overnight against 0.1M acetic acid buffer solution of pH 5.25 using a cellulose tube. The dialyzate was subjected to adsorption in a column (3.5 cm $\phi \times 45$ cm L) packed with CM-Sephadex C-50 equilibrated with the same buffer solution. Elution was conducted by the use of eluting solutions having a concentration gradient (0 to 0.5M) of sodium chloride. The active fractions eluted were collected and condensed. The condensate was dialyzed against 0.05M potassium phosphate buffer solution of pH 6.8 containing 0.1M sodium chloride using a cellulose tube. The dialyzate was subjected to gel filtration by the use of a column (2 cm $\phi \times 100$ cm L) packed with Sephadex G-200 equilibrated with the same buffer solution. The first half of the filtrate having a high relative activity was condensed, whereby 21 mg of purified N-acetylhexosamine oxidase was obtained. Yield: 4.1%; Relative activity: 15.5 unit/mg protein

What is claimed is:

1. An N-acetylhexosamine oxidase having the following physicochemical properties:
(1) action and specificity for substrate
  oxidizes N-acetylhexosamines including N-acetylglucosamine, N-acetylgalactosamine, N-acetylmuramic acid, N,N-diacetylchitobiose and N-acetylmannosamine in the presence of oxygen to form N-acetylhexosaminic acid and hydrogen peroxide (2) optimum pH and stable pH range when using a potassium phosphate buffer solution containing 0.1M glycine, said N-acetylhexosamine oxidase exhibits an optimum pH of 7.5 to 8.5 and a stable pH range of 3 to 9

(3) molecular weight has a molecular weight of about 140,000 to 150,000 when measured according to a gel filtration method using Sephadex G-200 by the use of 0.05M potassium phosphate buffer solution.

2. A process for producing an N-acetylhexosamine oxidase which comprises (a) culturing, in a medium, a bacterial strain Pseudomonas sp. No. 15-1 (FERM BP-227) or a variant or mutant thereof, having an ability to produce an N-acetylhexosamine oxidase and (b) collecting the N-acetylhexosamine oxidase from the culture products.

3. A process according to claim 2, wherein the medium contains carbon sources, nitrogen sources, inorganic matters and N-acetylhexosamine.

4. A process according to claim 2, wherein the culture is conducted at 20° to 40° C.

* * * * *